US00PP28684P3

(12) United States Plant Patent
Beekenkamp

(10) Patent No.: US PP28,684 P3
(45) Date of Patent: Nov. 21, 2017

(54) ***BEGONIA* PLANT NAMED 'BKPBEEFR'**

(50) Latin Name: *Begonia×hiemalis*
Varietal Denomination: BKPBEEFR

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 33 days.

(21) Appl. No.: 14/756,925

(22) Filed: Oct. 30, 2015

(65) Prior Publication Data

US 2017/0127594 P1 May 4, 2017

(51) Int. Cl.
*A01H 5/02* (2006.01)

(52) U.S. Cl.
USPC ..... Plt./348

(58) Field of Classification Search
USPC ..... Plt./348
See application file for complete search history.

*Primary Examiner* — Keith Robinson
(74) *Attorney, Agent, or Firm* — C. A. Whealy

(57) ABSTRACT

A new and distinct cultivar of *Begonia* plant named 'BKPBEEFR', characterized by its upright to outwardly spreading and mounded plant habit; freely basal branching habit; dark green-colored leaves; uniform and freely flowering habit; and double flowers with tepals and tepaloids that are bright pink in color with slightly fringed margins.

2 Drawing Sheets

Botanical designation: *Begonia×hiemalis*.
Cultivar denomination: 'BKPBEEFR'.

BACKGROUND OF THE INVENTION

The present invention relates to a new and distinct cultivar of *Begonia* plant, botanically known as *Begonia×hiemalis*, commercially referred to as Elatior *Begonia* and hereinafter referred to by the name 'BKPBEEFR'.

The new *Begonia* plant is a product of a planned breeding program conducted by the Inventor in Maasdijk, The Netherlands. The objective of the breeding program was to develop new freely branching and freely flowering *Begonia* plants with attractive double flowers.

The new *Begonia* plant originated from a cross-pollination made by the Inventor in September, 2011 of a proprietary selection of *Begonia×hiemalis* identified as code number 6500161, not patented, as the female, or seed, parent with a proprietary selection of *Begonia×hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in April, 2012.

Asexual reproduction of the new *Begonia* plant by vegetative tip cuttings in a controlled greenhouse environment in Maasdijk, The Netherlands since August, 2012 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEFR'. These characteristics in combination distinguish 'BKPBEEFR' as a new and distinct *Begonia* plant:

1. Upright to outwardly spreading and mounded plant habit.
2. Freely basal branching habit.
3. Dark green-colored leaves.
4. Uniform and freely flowering habit.
5. Double flowers with tepals and tepaloids that are bright pink in color with slightly fringed margins.

Plants of the new *Begonia* can be compared to plants of the female parent selection. Plants of the new *Begonia* differ primarily from plants of the female parent selection in the following characteristics:

1. Plants of the new *Begonia* have double flowers whereas plants of the female parent selection have single flowers.
2. Flower tepals and tepaloids of plants of the new *Begonia* are bright pink in color whereas flower tepals of plants of the female parent selection are salmon in color.

Plants of the new *Begonia* can be compared to plants of the male parent selection. Plants of the new *Begonia* differ primarily from plants of the male parent selection in the following characteristics:

1. Plants of the new *Begonia* have darker green-colored leaves than plants of the male parent selection.
2. Plants of the new *Begonia* have larger flowers than plants of the male parent selection.
3. Flower tepals and tepaloids of plants of the new *Begonia* are bright pink in color whereas flower tepals and tepaloids of plants of the male parent selection are pale pink in color.

Plants of the new *Begonia* can be compared to plants of the *Begonia×hiemalis* 'Berseko', not patented. In side-by-side comparisons conducted in Maasdijk, The Netherlands, plants of the new *Begonia* differ from plants of 'Berseko' in the following characteristics:

1. Plants of the new *Begonia* are bushier than and not as compact as plants of 'Berseko'.
2. Tepals and tepaloids of plants of the new *Begonia* are more fringed than tepals and tepaloids of plants of 'Berseko'.

Plants of the new *Begonia* can be compared to plants of the *Begonia×hiemalis* 'Elektra Pink', disclosed in U.S. Plant Pat. No. 18,967. In side-by-side comparisons conducted in Maasdijk, The Netherlands, plants of the new *Begonia* differ from plants of 'Elektra Pink' in the following characteristics:

1. Plants of the new *Begonia* are bushier than and not as compact as plants of 'Elektra Pink'.
2. Tepals and tepaloids of plants of the new *Begonia* are less fringed than tepals and tepaloids of plants of 'Elektra Pink'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEFR' grown in a container.

The photograph on the second sheet are close-up views of upper and lower surfaces of typical flowers and leaves of 'BKPBEEFR' and at the left center of the photograph is a close-up view of typical flower buds with pedicels.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia×hiemalis* 'BKPBEEFR'.

Parentage:

*Female, or seed, parent.*—Proprietary selection of *Begonia×hiemalis* identified as code number 6500161, not patented.

*Male, or pollen, parent.*—Proprietary selection of *Begonia×hiemalis* identified as code number 6500604, not patented.

Propagation:

*Type.*—By vegetative tip cuttings.

*Time to initiate roots.*—About 20 days at temperatures about 25° C.

*Time to produce a rooted young plant.*—About 35 to 36 days at temperatures about 21° C. to 23° C.

*Root description.*—Medium in thickness, fibrous; typically light brown in color, actual color of the roots is dependent on substrate composition, water quality, fertilizer type and formulation, substrate temperature and physiological age of roots; plants of the new *Begonia* have not been observed to form tubers.

*Rooting habit.*—Moderate freely branching; medium density.

Plant description:

*Plant and growth habit.*—Upright to outwardly spreading and mounded plant habit; plant shape roughly flattened globular; freely basal branching with about six basal branches developing per plant; moderately vigorous growth habit; moderate growth rate.

*Plant height.*—About 22 cm.

*Plant width.*—About 29.2 cm.

*Lateral branch description.*—Length: About 7.9 cm. Diameter: About 9 mm. Internode length: About 1.6 cm. Strength: Moderately strong. Aspect: About 40° from the vertical. Texture: Pubescent. Luster: Glossy. Color, developing: Close to 144A. Color, fully developed: Close to between 144A and 146D.

*Leaf description.*—Arrangement: Alternate, simple. Length: About 13 cm. Width: About 10.6 cm. Shape: Broadly ovate. Apex: Acute. Base: Unequal, hastate, slightly to moderately imbricate. Margin: Bi-serrate. Texture, upper surface: Smooth, glabrous; velvety. Texture, lower surface: Sparsely pubescent along veins. Luster, upper surface: Moderately glossy. Luster, lower surface: Slightly glossy. Venation pattern: Laciniate. Color: Developing leaves, upper surface: Close to between 147A and N199A. Developing leaves, lower surface: Close to 177A. Fully expanded leaves, upper surface: Darker than close to N189A; venation, close to 146A to 146B. Fully expanded leaves, lower surface: Close to 182A to 182B; venation, close to 146B to 146C. Petioles: Length: About 5.4 cm. Diameter: About 6 mm. Texture, upper and lower surfaces: Pubescent. Luster, upper and lower surfaces: Glossy. Color, upper surface: Close to 152A; distally, close to 183A. Color, lower surface: Close to 152A. Stipules: Quantity per leaf: Two. Length: About 9 mm. Width: About 9 mm. Shape: Broadly ovate. Apex: Obtuse. Base: Broadly cuneate. Margins: Entire. Color, upper and lower surfaces: Close to 145A and 145B.

Flower description:

*Flowering habit.*—Double rotate flowers arranged in axillary compound cymes; freely flowering habit with about three to four flowers per cyme and about 75 flowers developing per plant; flowers face upright to outwardly; most flowers are sterile male flowers and occasionally single female flowers develop.

*Fragrance.*—None detected.

*Natural flowering season.*—Plants begin flowering about 65 days after planting; long flowering period, plants flower freely and continuously from spring into the autumn in The Netherlands.

*Postproduction longevity.*—Individual flowers last about ten days on the plant; flowers not persistent; plants maintain good substance for about 20 to 30 days in an interior environment.

*Inflorescence height.*—About 18.4 cm.

*Inflorescence diameter.*—About 9.7 cm.

*Flower buds.*—Length: About 2.4 cm. Diameter: About 1 cm to 2.5 cm. Shape: Broadly obovate to flabellate; flattened. Color: Close to between 53D and 181C; towards the base, close to 174A.

*Male flowers.*—Diameter: About 6.7 cm. Depth: About 2.9 cm. Tepals: Quantity per flower and arrangement: Two, opposite. Length: About 3.5 cm. Width: About 3.9 cm. Shape: Broadly obovate to nearly orbicular. Apex: Obtuse to rounded. Margin: Irregularly finely serrate. Texture, upper surface: Smooth, glabrous; moderately velvety. Texture, lower surface: Smooth, glabrous; slightly velvety. Luster, upper surface: Matte. Luster, lower surface: Moderately glossy. Color: When opening, upper surface: Close to 63C; towards the base, close to 62D; towards the margins, tinged with close to 63B. When opening, lower surface: Close to 62A to 62B. Fully opened, upper surface: Close to 63C; towards the base, close to 62D; towards the margins, tinged with close to 63B; color does not fade with development. Fully opened, lower surface: Close to 181C; towards the margins, close to 185A to 185C; color does not fade with development. Tepaloids: Quantity per flower and arrangement: About 40 in multiple whorls. Length: About 1.9 cm to 3.3 cm. Width: About 1.2 cm to 3.7 cm. Shape: Obcordate. Apex: Rounded. Margin: Dentate. Texture, upper and lower surfaces: Smooth, glabrous; moderately velvety. Luster, upper and lower surfaces: Matte. Color: When opening, upper and lower surfaces: Close to 62A; towards the margins, close to 63B. Fully opened, upper and lower surfaces: Close to 62C; towards the margins, close to 62A; color does not fade with development.

*Female flowers.*—Diameter: About 5 cm. Depth: About 1.8 cm. Tepals: Quantity per flower and arrangement: Six, arranged in a single whorl. Length: About 2.3 cm. Width: About 2.6 cm. Shape: Broadly obovate to nearly orbicular. Apex: Obtuse to rounded. Margin: Entire. Texture, upper surface: Smooth, glabrous; moderately velvety. Texture, lower surface: Smooth, glabrous; slightly velvety. Luster, upper surface: Matte. Luster, lower surface: Moderately glossy. Color: When opening, upper surface: Close to 62B; towards the margins, close to 63B. When opening, lower surface: Close to 181 C. Fully opened, upper surface: Close to 62A; color does not fade with development. Fully opened, lower surface: Close to 181D; color does not fade with development. Tepaloids: None observed on female flowers.

*Peduncles, male and female flowers.*—Length: About 9.1 cm. Diameter: About 5.5 mm. Angle: About 45° from lateral branch axis. Strength: Moderately strong; flexible and bending with the weight of the flowers. Texture: Sparsely pubescent. Luster: Moderately glossy. Color: Close to 144A.

*Pedicels, male and female flowers.*—Length: About 3.4 cm. Diameter: About 3 mm. Angle: About 20° to 45° from the peduncle axis. Strength: Moderately strong; flexible, bending with the weight of the flowers. Texture: Smooth, glabrous. Luster: Moderately glossy. Color: Close to 176A.

*Flower bracts.*—Quantity per flower: Two. Length: About 1.4 cm. Width: About 1.9 cm. Shape: Orbicular to reniform. Margin: Entire. Texture, upper and lower surfaces: Smooth, glabrous; moderately velvety. Luster, upper and lower surfaces: Moderately glossy. Color, upper and lower surfaces: Close to 144A; towards the margins, close to 185A.

*Reproductive organs.*—Androecium: All stamens transformed into tepaloids on male flowers. Gynoecium: Present only on female flowers. Quantity per flower: Six, fused in pairs. Pistil length: About 7 mm. Stigma shape: Spiral. Stigma color: Close to 9A. Style length: About 5.5 mm. Style color: Close to 145B to 145C. Ovary color: Close to 146C strongly tinged with close to 178A to 178B. Seeds and fruits: Seed and fruit development have not been observed on plants of the new *Begonia.*

Disease & pest resistance: Resistance to pathogens and pests common to *Begonia* plants has not been observed on plants of the new *Begonia.*

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEEFR' as illustrated and described.

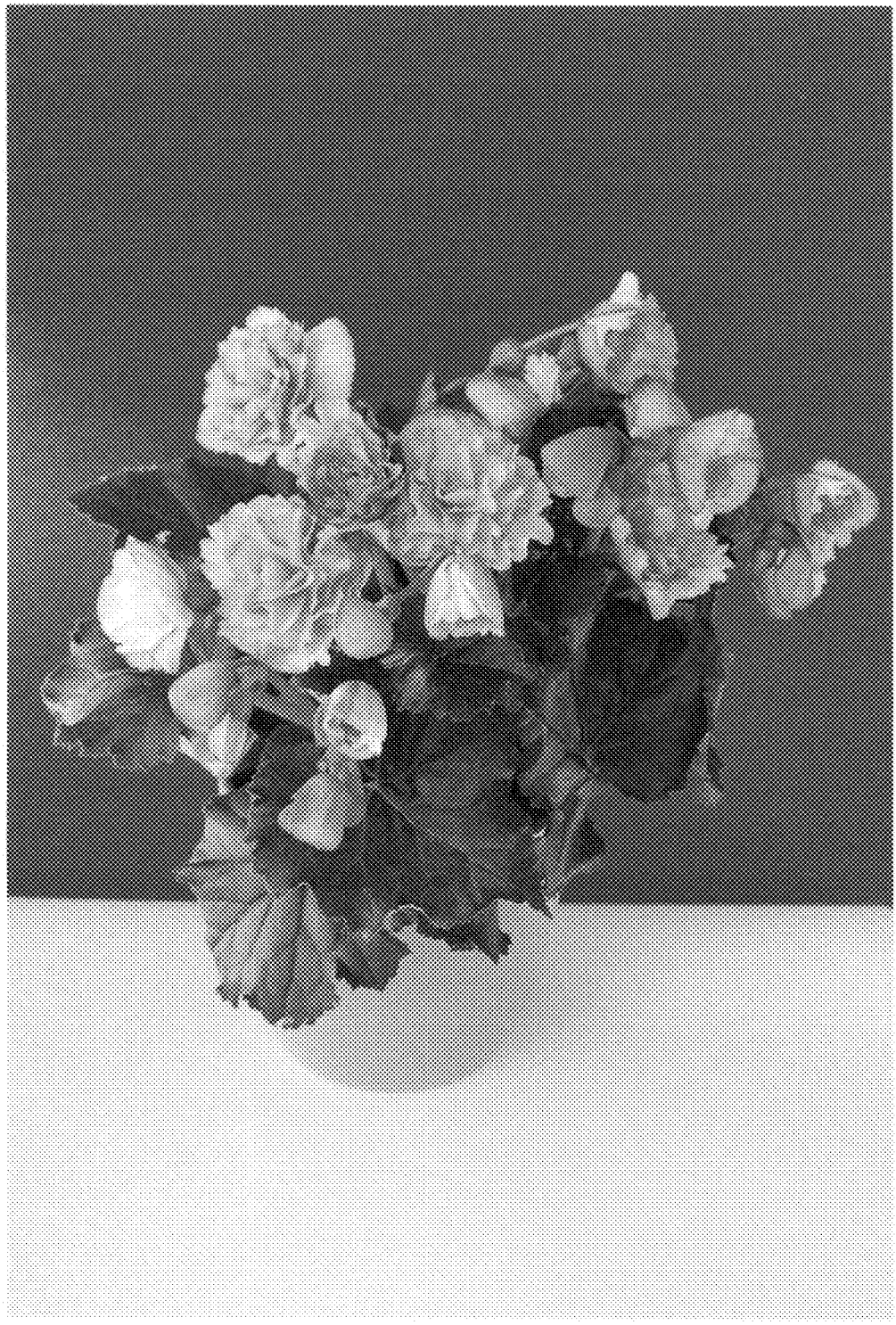

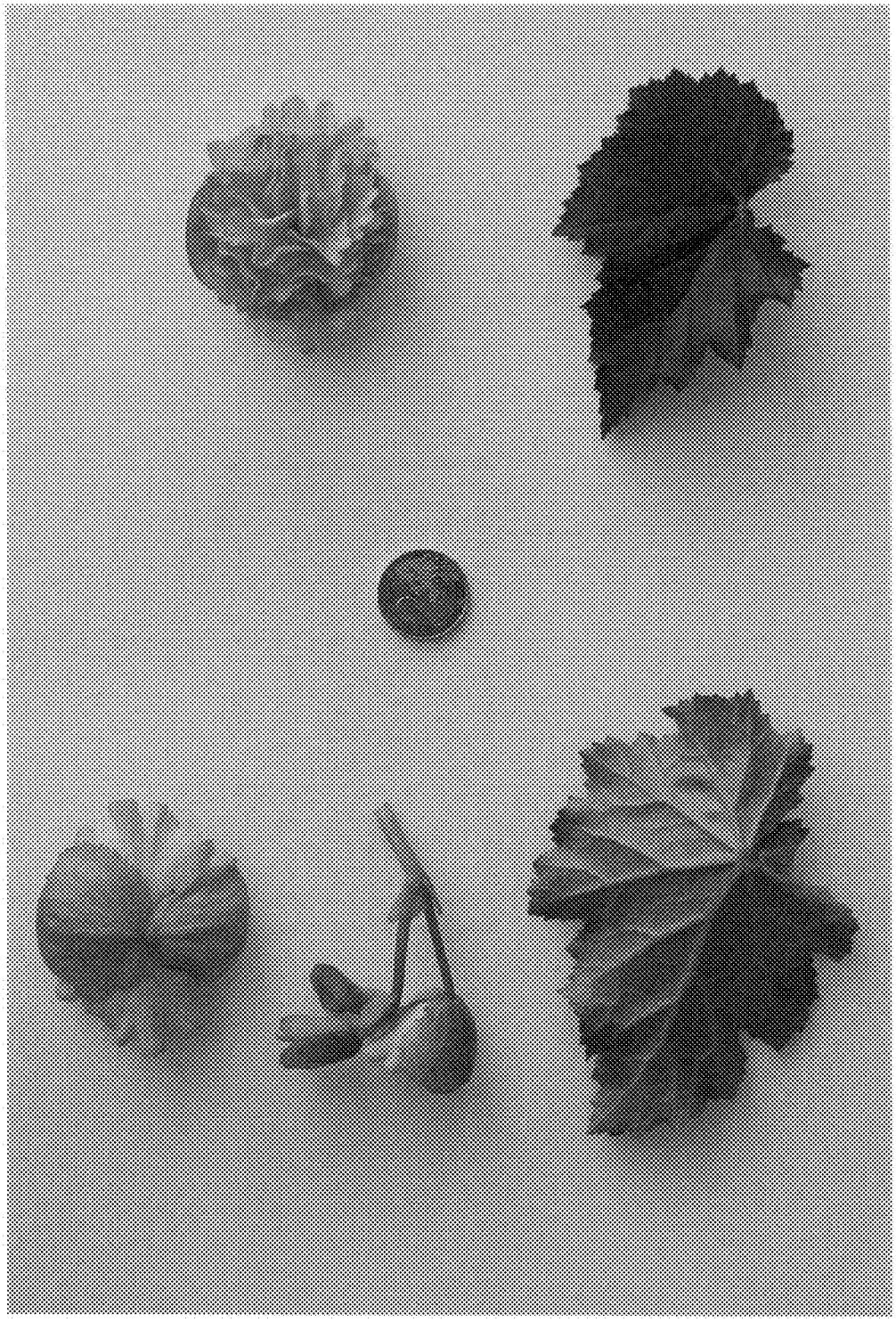

* * * * *